(12) United States Patent
Harbut et al.

(10) Patent No.: US 11,363,985 B2
(45) Date of Patent: Jun. 21, 2022

(54) SYSTEMS AND METHODS FOR PAIN TRACKING

(71) Applicant: Nanolume, LLC, Hot Springs, AR (US)

(72) Inventors: Ronald E. Harbut, Hot Springs, AR (US); Chris Rouw, Cedar Falls, IA (US)

(73) Assignee: Nanolume, LLC, Hot Springs, AR (US)

( * ) Notice: Subject to any disclaimer, the term of this patent is extended or adjusted under 35 U.S.C. 154(b) by 990 days.

(21) Appl. No.: 15/130,712

(22) Filed: Apr. 15, 2016

(65) Prior Publication Data

US 2016/0306946 A1 Oct. 20, 2016

Related U.S. Application Data

(60) Provisional application No. 62/149,396, filed on Apr. 17, 2015.

(51) Int. Cl.
| | |
|---|---|
| *A61B 5/00* | (2006.01) |
| *A61N 1/372* | (2006.01) |
| *G16H 10/60* | (2018.01) |
| *A61N 1/36* | (2006.01) |

(Continued)

(52) U.S. Cl.
CPC ........ *A61B 5/4824* (2013.01); *A61N 1/37247* (2013.01); *A61N 1/36071* (2013.01); *G09B 23/28* (2013.01); *G16H 10/60* (2018.01); *G16H 20/30* (2018.01)

(58) Field of Classification Search
CPC .... G06Q 10/10; G06Q 10/1093; G06Q 10/00; G06Q 30/02; G06Q 30/0269; G06Q 40/08; G06Q 10/0635; G06Q 10/0639
See application file for complete search history.

(56) References Cited

U.S. PATENT DOCUMENTS

2002/0030682 A1* 3/2002 Eberlein ................ G16H 10/20
345/440
2004/0267099 A1* 12/2004 McMahon ............... A61B 5/00
600/300

(Continued)

OTHER PUBLICATIONS

Lynn, Damon."My Pain Diary: Chronic Pain & Symptom Tracker", Apple iTunes App Store, 2009. Updated Mar. 10, 2016, version 3.5.8, pp. 1-3.

(Continued)

*Primary Examiner* — Rachel L. Porter
(74) *Attorney, Agent, or Firm* — Dentons Durham Jones Pinegar

(57) ABSTRACT

Systems, methods, and computer program products for recording and monitoring pain are disclosed. A device may record a date and time corresponding to a pain entry, a pain type corresponding to the pain entry, and a pain intensity corresponding to the pain entry. The device may further record a pain location on a body corresponding to the pain entry. The device may also display the pain entry. In various embodiments, the device may display a graphical pain representation superimposed over the pain location on the body. The device may also read an input encircling the pain location on the body. The device may further display a plurality of pain entries in a plot relative to time.

19 Claims, 8 Drawing Sheets

(51) Int. Cl.
    *G09B 23/28* (2006.01)
    *G16H 20/30* (2018.01)

(56) References Cited

U.S. PATENT DOCUMENTS

| | | | | |
|---|---|---|---|---|
| 2009/0005649 | A1* | 1/2009 | Baird | A61B 5/00 |
| | | | | 600/300 |
| 2013/0073306 | A1* | 3/2013 | Shlain | G16H 10/20 |
| | | | | 705/2 |
| 2013/0218541 | A1* | 8/2013 | Dodson | G16H 10/20 |
| | | | | 703/2 |
| 2015/0324544 | A1* | 11/2015 | Maslowski | A61B 6/032 |
| | | | | 600/409 |
| 2016/0220178 | A1* | 8/2016 | Rigoard | G06F 3/04845 |
| 2018/0008191 | A1* | 1/2018 | Cronin | G16H 40/63 |

OTHER PUBLICATIONS

Sanovation AG, "Pain Diary & Community CatchMyPain Incl. Medication Tracker", Apple iTunes App Store, 2014. Updated Mar. 15, 2016, Version 3.5.6, pp. 1-3.

Chronic Stimulation, LLC, "Chronic Pain Tracker", Apple iTunes App Store, 2009. Updated Mar. 17, 2016, Version 3.8.2, pp. 1-3.

Symple Health, Inc., "Symple-Symptom Tracker & Health Diary", Apple iTunes App Store, 2016. Updated Apr. 6, 2016, Version 2.0.8, pp. 1-3.

Delaporte, Ben. "Chronic Pain Diary", Apple iTunes App Store, 2012. Updated Jan. 10, 2014, Version 1.16, pp. 1-3.

* cited by examiner

SYSTEMS AND METHODS FOR PAIN TRACKING

CROSS REFERENCE TO RELATED APPLICATIONS

This application claims priority to and the benefit of U.S. Provisional Patent Application Ser. No. 62/149,396 filed Apr. 17, 2015 entitled "SYSTEMS AND METHODS FOR PAIN TRACKING." The aforementioned application is hereby incorporated by reference herein in its entirety.

FIELD

The present disclosure generally relates to pain tracking, and more particularly to systems and methods for tracking and analyzing pain using an electronic device.

BACKGROUND

People often experience physical pain. Pain can be acute (lasting less than 3-6 months) or it can be chronic (lasting longer than 3-6 months). Bruises, scrapes, strains, and trauma, for example, can all result in different types and/or intensities of pain.

Pain is a complex unpleasant sensation that can constantly change with varying intensities, textures, locations, degrees and patterns of spread. Pain is typically expressed subjectively by the patient experiencing the pain. The varying types, intensities, locations, degrees and patterns of pain a person feels may or may not be readily communicable at the time a person is experiencing the pain. In addition, a person's memory of the complexities of pain experienced can become less clear. As the patient's ability to accurately recall his or her past history of pain becomes increasingly more difficult, important historical details may not be provided to their doctor during their appointments. Many patients experiencing chronic pain struggle to consistently and accurately catalogue their pain.

Doctors typically diagnose and treat pain based on the information provided to them by the patient. When a patient's pain history is inaccurate or incomplete, a doctor's treatment plan, both current and long term, will be based on imperfect information. The consequence of imperfect information can lead to inaccurate diagnoses, imperfect treatment plans, and prolonged or increasing pain and suffering.

SUMMARY

Systems, methods, and computer-readable media for recording pain are disclosed. In various embodiments, a device may record a date and time corresponding to a pain entry, a pain type corresponding to the pain entry, and a pain intensity corresponding to the pain entry. The device may further record a pain location on a body corresponding to the pain entry. The device may also display the pain entry. The device may display a graphical pain representation superimposed over the pain location on the body. The device may also read an input encircling the pain location on the body. The device may further display a plurality of pain entries in a plot relative to time.

BRIEF DESCRIPTION OF THE DRAWINGS

A more complete understanding may be derived by referring to the detailed description and claims when considered in connection with the Figures, wherein like reference numbers refer to similar elements throughout the Figures, and:

DETAILED DESCRIPTION

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

Systems, methods and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. After reading the description, it will be apparent to one skilled in the relevant art(s) how to implement the disclosure in alternative embodiments.

Systems and methods are disclosed herein for peer to peer communication between communication devices. As used herein, an "electronic device" may refer to any device capable of accepting, storing, and processing data. For, example and without limitation, an electronic device may refer to a smartphone, PDA, laptop, desktop computer, portable phone, GPS device, car navigation system, or any other suitable device.

Figure 1:
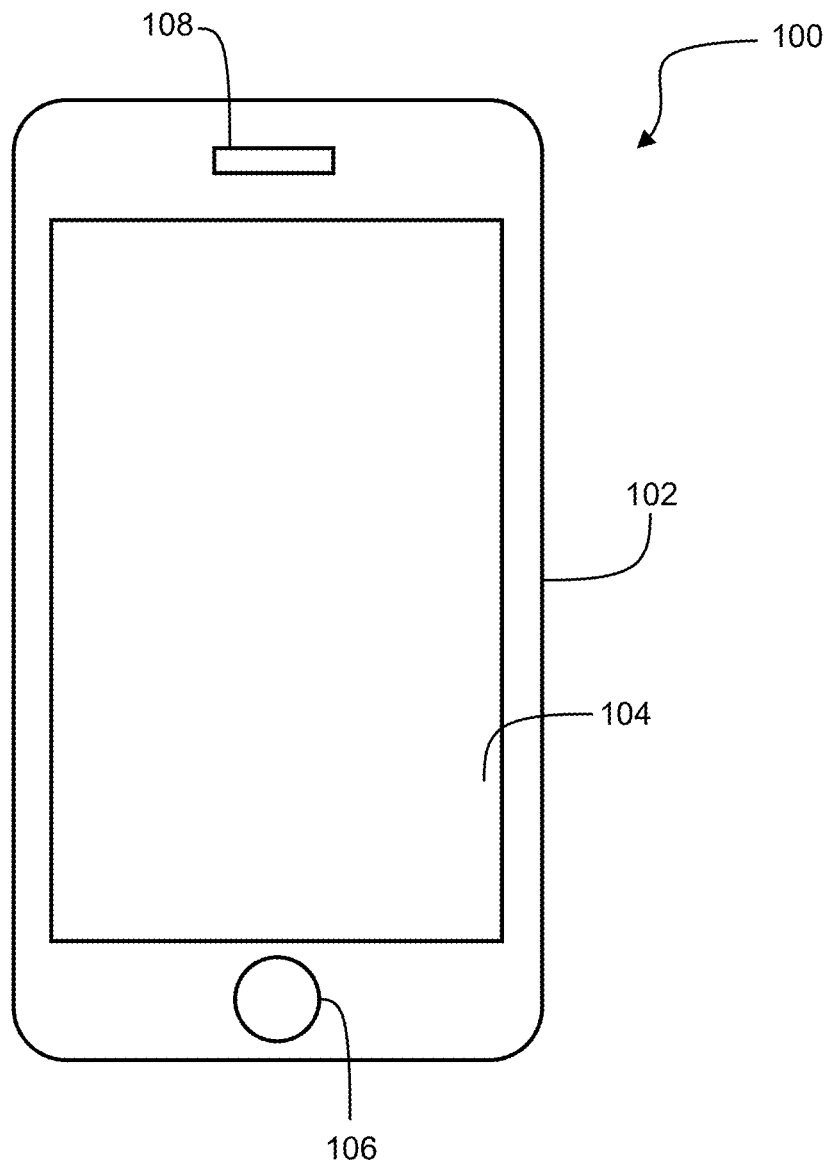
FIG. 1 illustrates an exemplary electronic device for use tracking and monitoring pain according to various embodiments of the disclosure.

With reference to FIG. 1, an exemplary electronic device 100 is shown according to various embodiments. Electronic device 100 as depicted is a touch screen device such as a smart phone or tablet. Electronic device 100 may comprise a housing 102 providing support for various input and output devices. Screen 104 may be a glass display embedded in housing 102 and capable of reading touch input. For example, screen 104 may comprise a capacitive touchscreen with a conductor coated over a glass insulator. Electronic device 100 may also include an input button 106 and a speaker 108 for an output. The various input and output structures of electronic device 100 enable electronic device 100 to accept and respond to user input as well as provide visual or audible output.

Electronic device 100 may include one or more of the following: a computing system including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: pain data; user data; illustrative data; and/or like data useful in the operation of the system. As those skilled in the art will appreciate, the user computer may include an operating system (e.g., Windows, OSX, iOS, UNIX, Linux, MacOS, Android, etc.) as well as various conventional support software and drivers typically associated with computers.

Figure 2:
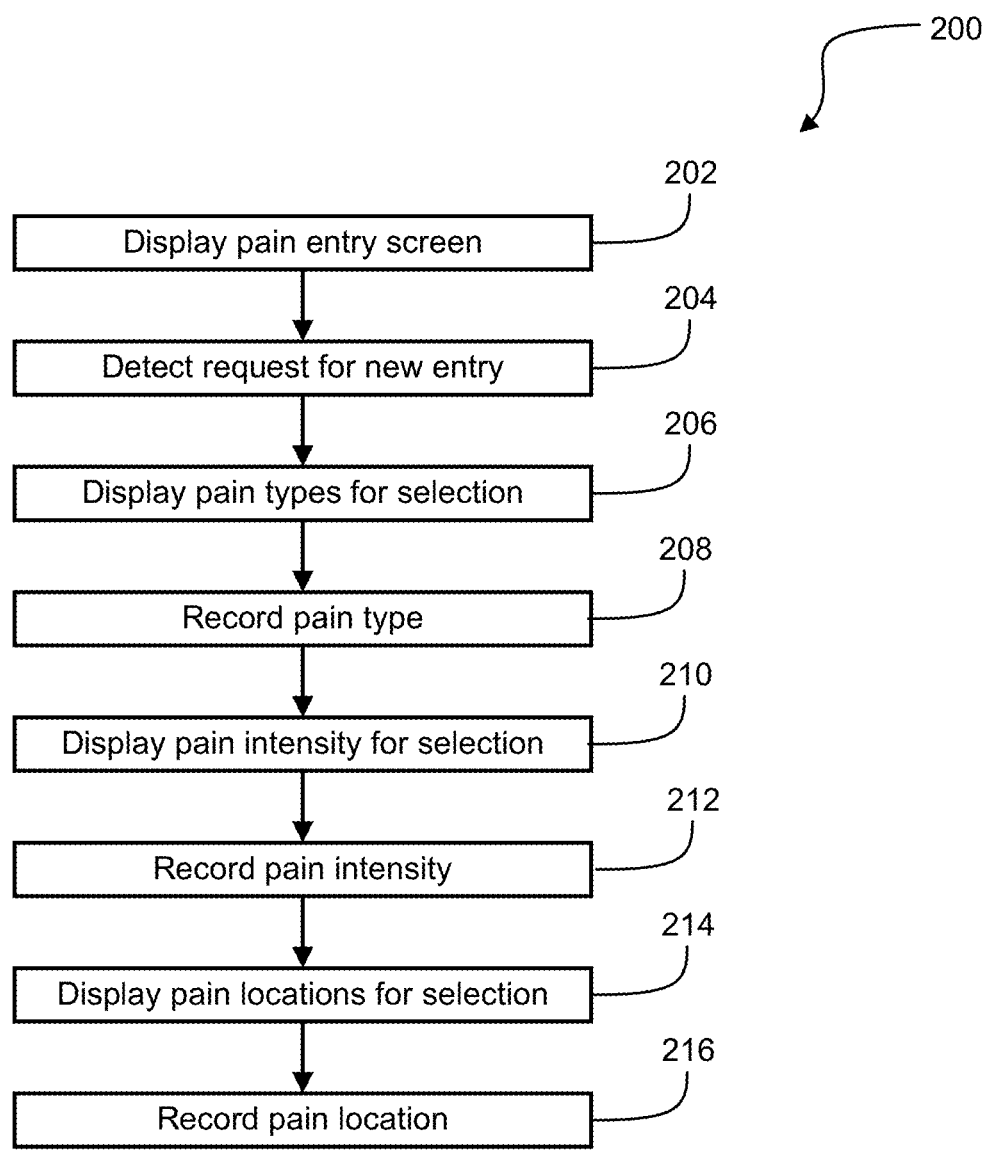
FIG. 2 illustrates a process for collecting and storing pain data in an electronic format according to various embodiments of the disclosure.
Figure 3:
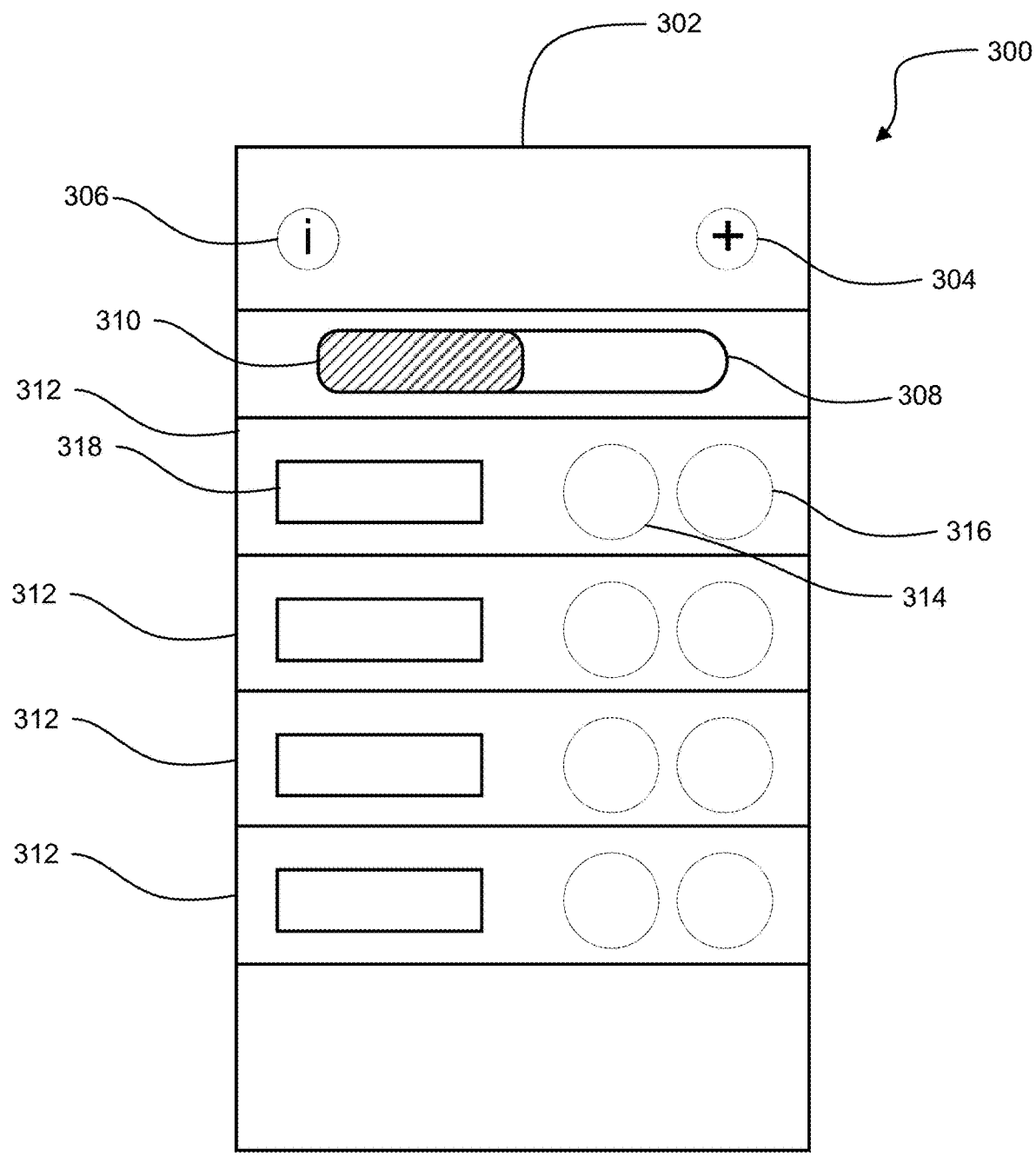
FIG. 3 illustrates an interface for collecting pain data in an electronic format according to various embodiments of the disclosure.

With reference to FIG. 2, a process 200 for recording pain data using an electronic device 100 of FIG. 1 is shown, in accordance with various embodiments. Process 200 may begin by displaying a pain entry screen (Step 202). Referring to FIG. 3, the pain entry screen 300 may include a title portion 302. Title portion 302 may comprise interface buttons. For example, button 304 and button 306 may be rendered on screen 104. Instructions may be displayed in response to button 306 being touched, and a new pain entry may be created in response to button 304 being touched. Pain entry screen 300 may also comprise pain entries 312 and a selection interface 308. In the illustrated example, the selection button 310 is slid to the left to display a list of pain entries 312.

With reference to FIGS. 2 and 3, the process may further include detecting a request for a new pain entry (Step 204). Each pain entry 312 may include a date and time 318, pain intensity 314, and/or a coverage area 316. Coverage area 316 may refer to the percentage of the body surface "covered" in pain. Each pain entry may be entered by pressing button 304 and completing one or more steps of process 200. Entries may be created at varying times and dates to record pain experienced by a user.

Figure 4:
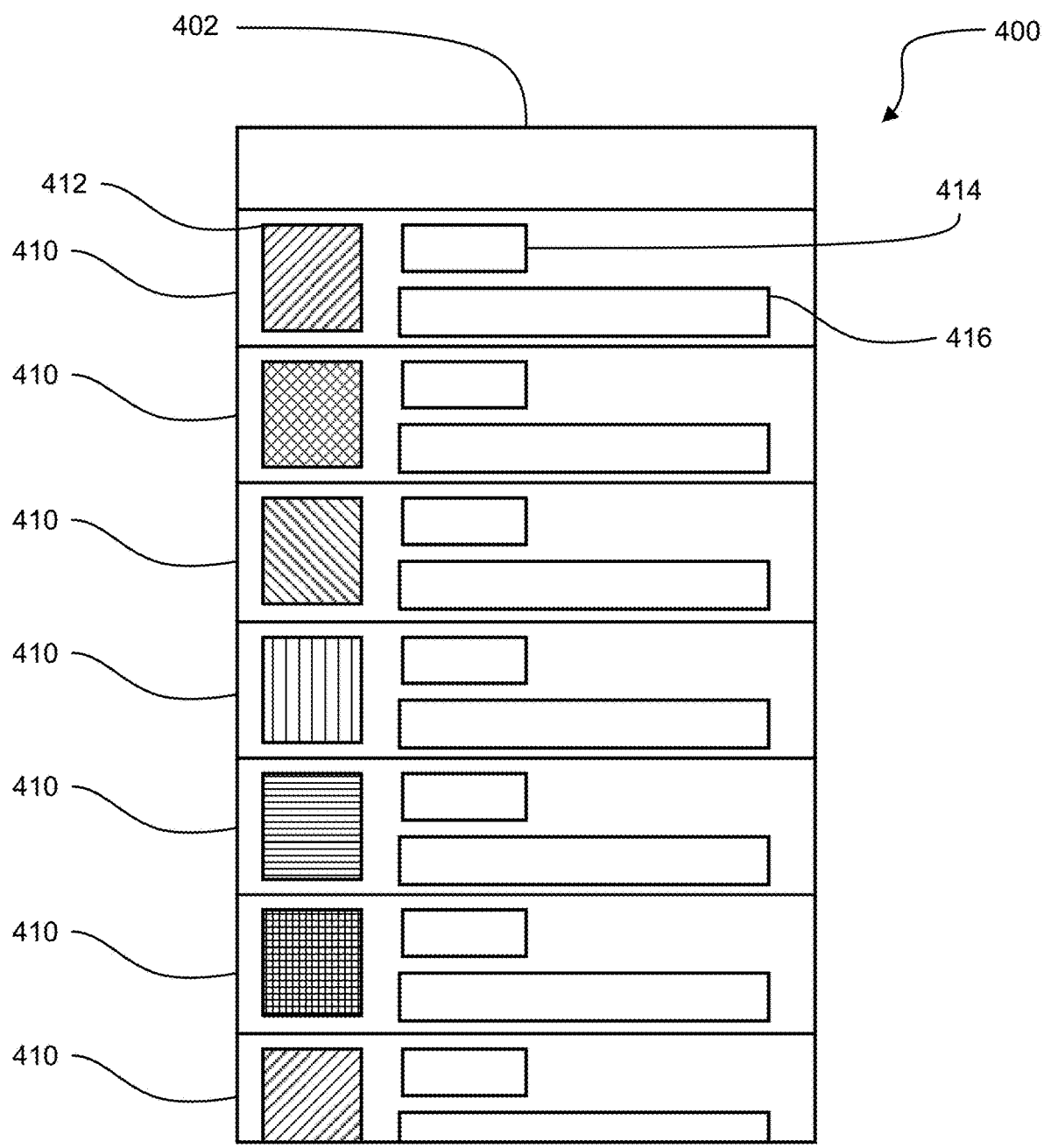
FIG. 4 illustrates an interface for selecting a pain type according to various embodiments of the disclosure.

Referring to FIGS. 2 and 4, pain types 410 may be displayed on pain type screen 400 in response to the request for a new entry (Step 206). Pain type screen 400 may include a title portion 402. Title portion 402 may include a title, for example, "Pain Type." Title portion 402 may also include instructions for a user to select a pain type. A list of pain types 410 may be displayed beneath the title portion.

In various embodiments, pain types 410 may include pain descriptors 414 such as aching, allodynia, burning, cutting, freezing, shooting, squeezing, stabbing, stiffness, stretching, throbbing, tingling, and/or any other suitable pain descriptor. Each pain descriptor 414 may have a corresponding description 416. The description 416 may be a plain-language definition of the corresponding pain descriptor 414. Exemplary pain descriptors 414 and descriptions 416 corresponding to pain descriptors 414 are listed in table T1 below.

TABLE T1

Exemplary pain descriptors 414 and corresponding descriptions 416.

| Pain Descriptor | Description |
| --- | --- |
| Aching | A dull, heavy, hurting-type of soreness. |
| Allodynia | An unusual skin-sensitivity to light touch or vibrations that causes severe pain. |
| Burning | A fiery, blistering, broiling, or searing pain. |
| Cutting | A sharp, tearing, or lacerating pain. |
| Freezing | A shivering, bone-chilling, or ice-cold sensation. |
| Numbness | A decrease in the sensation of touch, temperature, and/or pressure. |
| Shooting | A flash of pain that travels across or down a body region. |
| Squeezing | A pinching, compressing, crushing, spasm-like, or squashing pain. |
| Stabbing | A prickling, boring, drilling, knife-like, or lancinating pain. |
| Stiffness | An inability to move a joint or muscle due to tightness or poor flexibility. |
| Stinging | A sharp, pinching, pins-and-needles pain. |
| Stretching | A pulling, twisting, tugging pain. |
| Throbbing | A grabbing, pulling, twisting, tugging, or wrenching pain. |
| Tingling | An itchy, pins-and-needles, or stinging pain. |

In various embodiments, each pain descriptor 414 and description 416 in a pain type 410 is matched to a graphical pain representation 412. Graphical pain representation 412 may be used in locating pain in subsequent steps. Each graphical pain representation 412 may comprise a unique design and/or color relative to other graphical pain representations 412. For example, the pain descriptor 414 of "burning" may be represented by an orange flame-shaped pattern while the pain descriptor 414 for "freezing" may be represented by a blue snowflake pattern. Graphical pain representations 412 may provide a graphical identifier when superimposed over a body for the location of each pain type, as discussed in further detail below.

In various embodiments, a user may scroll through the list of pain types 410 to identify a pain type for recording. If electronic device 100 of FIG. 1 is a touch-screen device then a user may a touch pain type 410 displayed on screen 104 to select the pain type 410. Electronic device 100 may then record the selected pain type (Step 208). The selected pain type may be stored on a permanent storage component integrated into and/or connected to electronic device 100 such as a solid state drive or a hard drive using, for example, a database, a flat file, or another suitable data storage structure. Cloud storage and/or remote storage may also be used provided security precautions are taken to maintain user privacy.

Figure 5:
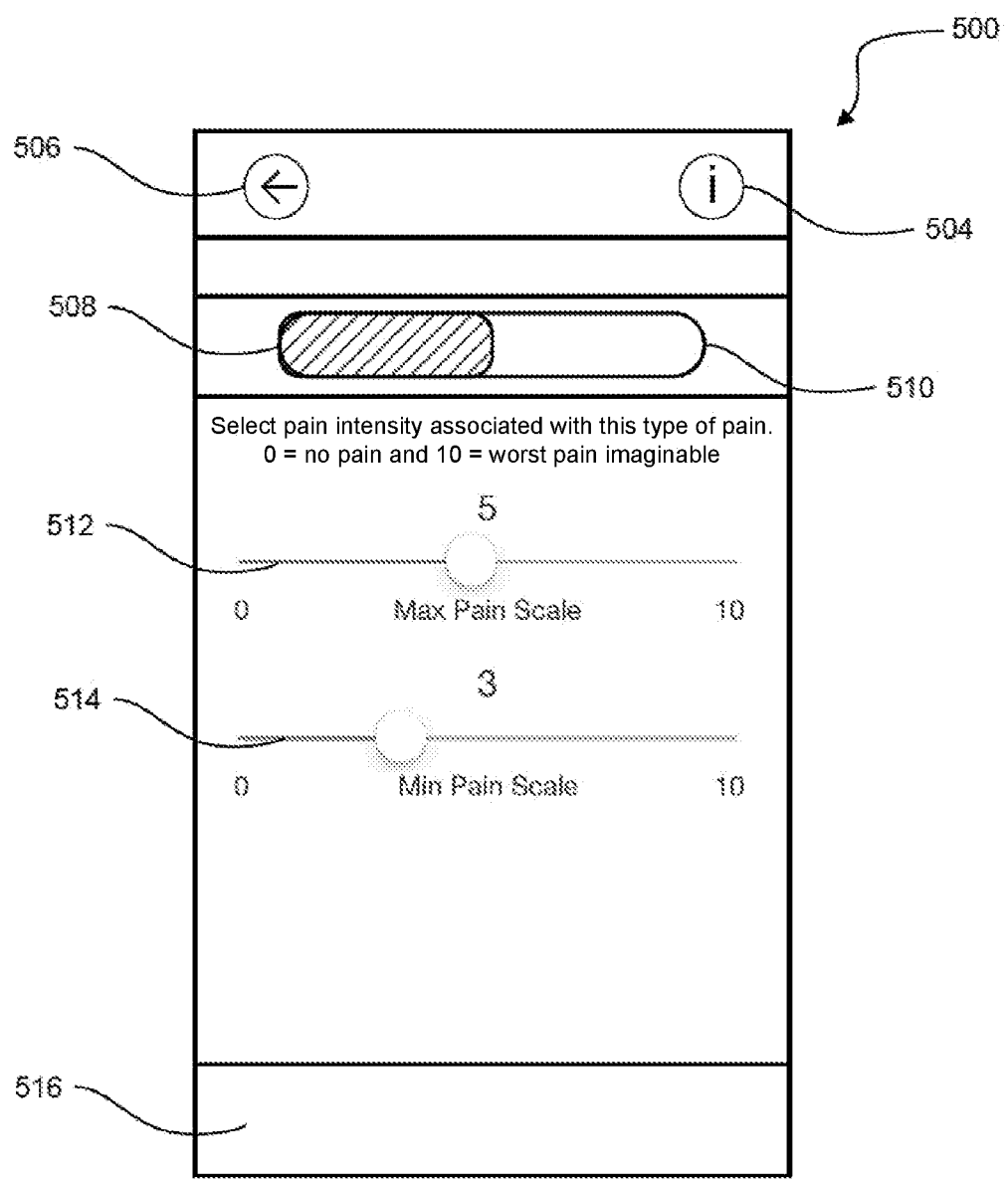
FIG. 5 illustrates an interface for inputting pain intensity according to various embodiments of the disclosure.

With reference to FIGS. 2 and 5, pain intensities may be displayed on pain intensity screen 500 for selection (Step 210). Pain intensity screen 500 may comprise input buttons such as information button 504 and back button 506. Back button 506 may take a user back to previous screens and/or steps in response to being pressed. Information button 504 may provide information in response to being pressed. A pain evaluation on the 1 to 10 scale may be provided. Selection button 510 may have selector 508 positioned to the left to indicate that a user wants to enter a minimum pain intensity 514 and maximum pain intensity 512. Selection button 510 may also have selector 508 positioned to the right to enter an individual pain intensity rather than a range.

In various embodiments, the maximum pain intensity 512 may represent a highest pain experienced by a user while the minimum pain intensity 514 may represent the least pain experienced by the user at the time of entry. Maximum pain intensity 512 and minimum pain intensity 514 (or any other pain intensity) may be entered using a sliding scale, a text box, or another suitable interface to enter an integer. With the desired pain intensities input into electronic device 100, the user may press completion button 516 to indicate completion. Electronic device 100 may then record pain intensity (Step 212) corresponding to the previously recorded pain type (in Step 208).

Figure 6:
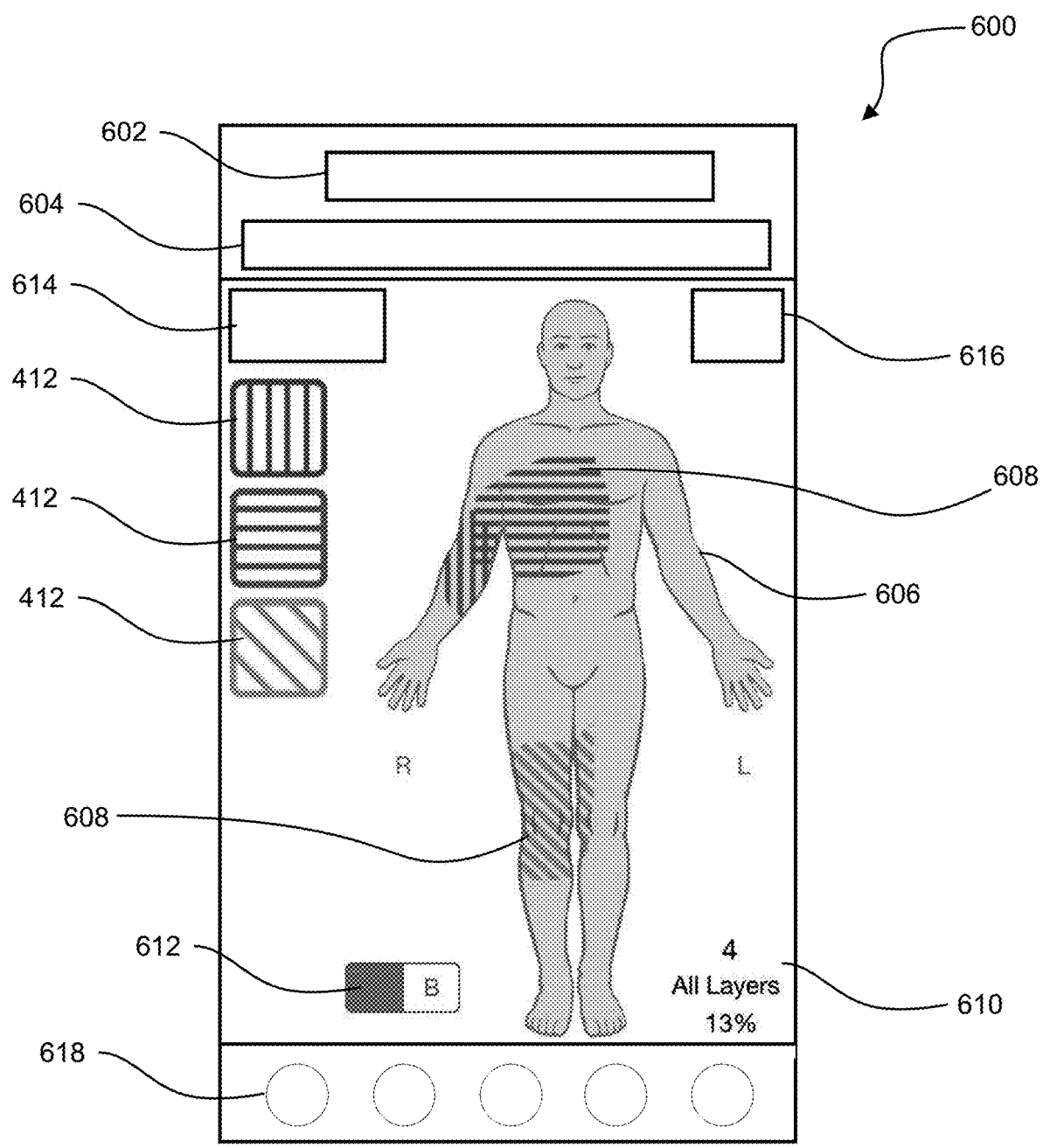
FIG. 6 illustrates an interface for inputting a pain location according to various embodiments of the disclosure.

With reference to FIGS. 2 and 6, pain locations may be displayed on pain location screen 600 for selection (Step 214). Pain location screen 600 may include a title portion 602 with a title such as "Pain Location" and/or instructions such as "Draw Your Pain." The date and time 604 may be displayed and may be the entry date corresponding to the pain entry presently being created. The graphical pain representation 412 corresponding to a selected pain type 410 (in FIG. 4) may be displayed on pain location screen 600. The pain may be located on body 606 by superimposing graphical pain representation 412 over body 606 to indicate the location at which a subject is experiencing pain. Graphical pain representations 412 may be added to body 606 at pain locations 608 by drawing and/or encircling the pain location 608. For example, if electronic device 100 is a touch screen device, then pain location 608 may be encircled on the screen using a finger and/or stylus. Pain location 608 for each pain type 410 may thus be located.

Referring to FIGS. 3 and 6, coverage area 316 for each distinct pain entry 312 and/or all pain types (total body pain, i.e., All Layers) may be calculated by counting the number of "points" contained in the image of the body. The number of points on the images of the front and back of body (e.g., body 606, discussed below with reference to FIG. 6). These point collections are stored in local memory for later calculations.

The coverage area 316 might be different for each of the pain entries 312 a patient is experiencing. A patient may have some pain-types that do not overlap, some that partially overlap, or some that completely overlap with reference to position on the body 606, as shown in FIG. 6. Each distinct pain entry 312 may be mapped by the patient to the area on body 606 where the patient is experiencing pain. In that regard, a surface area may be precisely displayed representing the coverage area 316 of each distinct pain-type separately as requested. Coverage areas may also be displayed in aggregate, (i.e., the total surface area of the body covered by pain).

In various embodiments, a user may display an individual pain location 608 corresponding to graphical pain representation 412 by clicking or touching the graphical pain representation 412. The user may display all graphical pain representations 412 at pain locations 608 on body 606 by pressing the button 614 to select all layers. A user may further view a back side of body 606 by toggling front/back selection interface 612. In this manner, pain locations 608 may be placed and/or viewed on a back side of body 606. Additional pain layers may be added by pressing and/or touching add pain input 616. Electronic device 100 may then return the user to step 206 to add an additional pain type to body 606 in response to add pain input 616.

In various embodiments, pain location screen 600 may further include information display 610. Information display 610 may display a weighted mean or average of the pain intensity, the layers being displayed, and the percentage of body 606 covered by pain locations 608 (i.e., coverage area 316) for an individual graphical pain representation 412 or for all graphical pain representations 412. Interface buttons 618 may further be included on pain location screen 600. Interface buttons 618 may include options to delete, edit, erase, undo, or finish editing information that has been input on pain location screen 600. A user may press a "done" button to indicate that pain locations 608 have been placed. Pain locations 608 may be recorded (Step 216) in response to the placement of pain locations 608. In that regard, pain may be tracked, mapped, and monitored over time.

Figure 7:
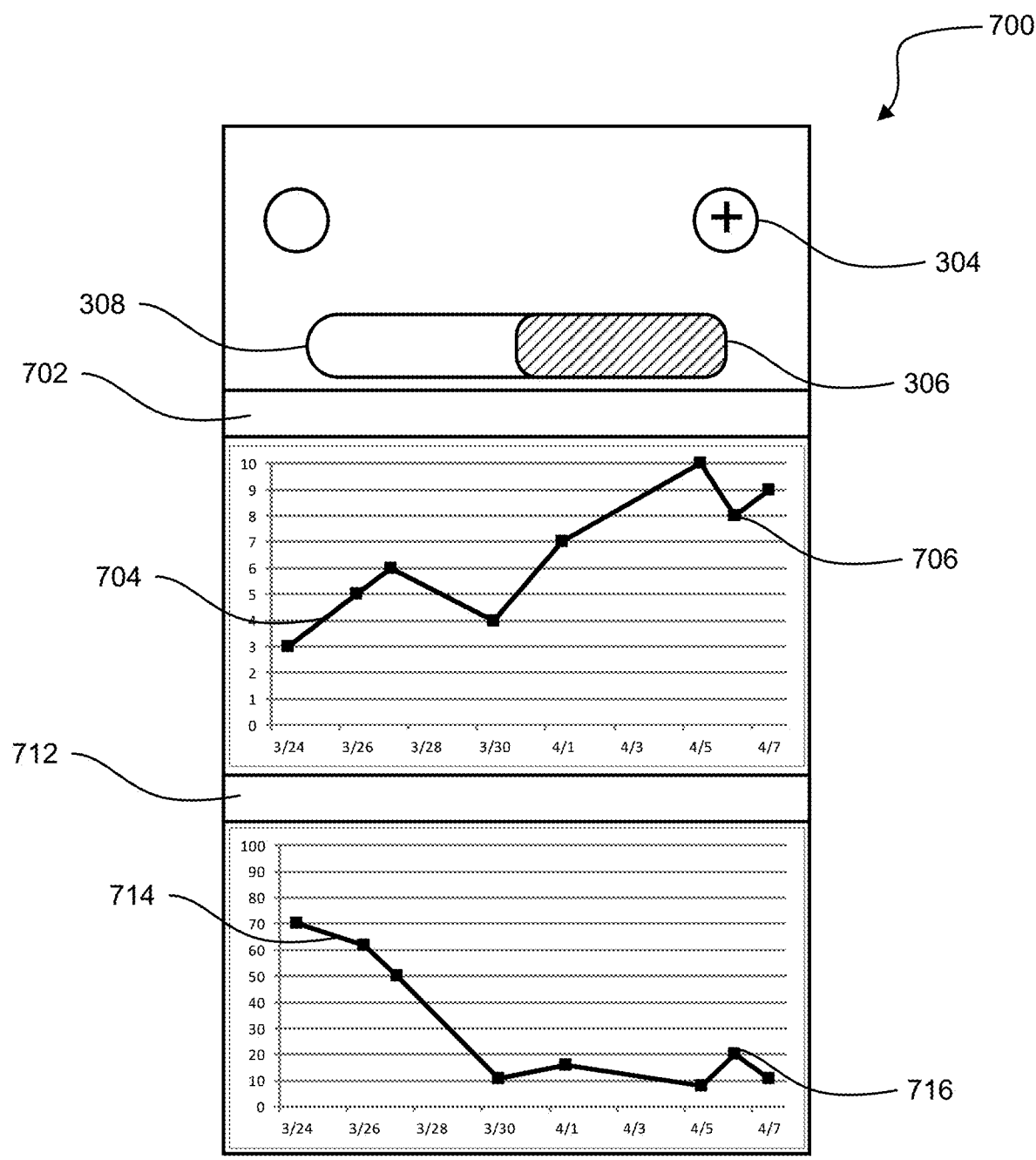
FIG. 7 illustrates an interface for displaying pain information over time according to various embodiments of the disclosure.

In various embodiments, and with reference to FIG. 3, the user may be returned to pain entry screen 300. A pain entry 312 may be displayed with the date and time 318, a pain intensity 314 (as recorded in Step 210 of FIG. 2), and/or a coverage area 316 (as recorded in Step 216 of FIG. 2). With reference to FIG. 7, the selection button 310 may be slid to the right of selection interface 308 to switch between displaying trends in pain over time and displaying a list of pain entries. When applicable, a user may alter body 606 to accommodate patients who have an amputated limb to make body 606 representative of such patients. Coverage area 316 may be adjusted accordingly.

With continuing reference to FIG. 7, trend display screen 700 is shown with graphical trends. Trend display screen 700 may include interface buttons such as button 304, which a user may press to create a new pain entry. Trend display screen 700 may further include one or more plots of pain entries 312. Title 702 may be descriptive of plot 704. Plot 704 may be a graphical representation of each pain entry 312 in terms of pain intensity 314 relative to date and time 318 the pain entry containing pain intensity 314 was created. Each point 706 on plot 704 is located based on the (x, y) pair of (date and time 318, pain intensity 314). On the X axis, point 706 is located with date and time 318 of pain entry 312 chronologically increasing from left to right. Point 706 is located on the Y axis based on pain intensity 314. Pain intensity 314 may be a weighted mean of pain intensities and may be rounded to a nearest integral number or located in decimal form, depending on the desired accuracy. In that regard, plot 704 may illustrate changes in pain intensity over time. Title 702 of plot 704 may thus be "Pain Intensity," for example.

In various embodiments, electronic device 100 may display a plurality of pain entries 312 in plot 714 relative to date and time 318. Title 712 may be descriptive of plot 714. Each point 716 may be located based on the (x, y) pair of (date and time 318, coverage area). On the X axis, point 716 is located with date and time 318 of pain entry 312 chronologically increasing from left to right. Point 716 is located on the Y axis based on the coverage area 316. Coverage area 316 may be estimated by taking the surface area of the body 606 marked with pain divided by the total body surface area. In that regard, plot 714 may illustrate changes in the surface area of the body subject to pain over time.

Figure 8:
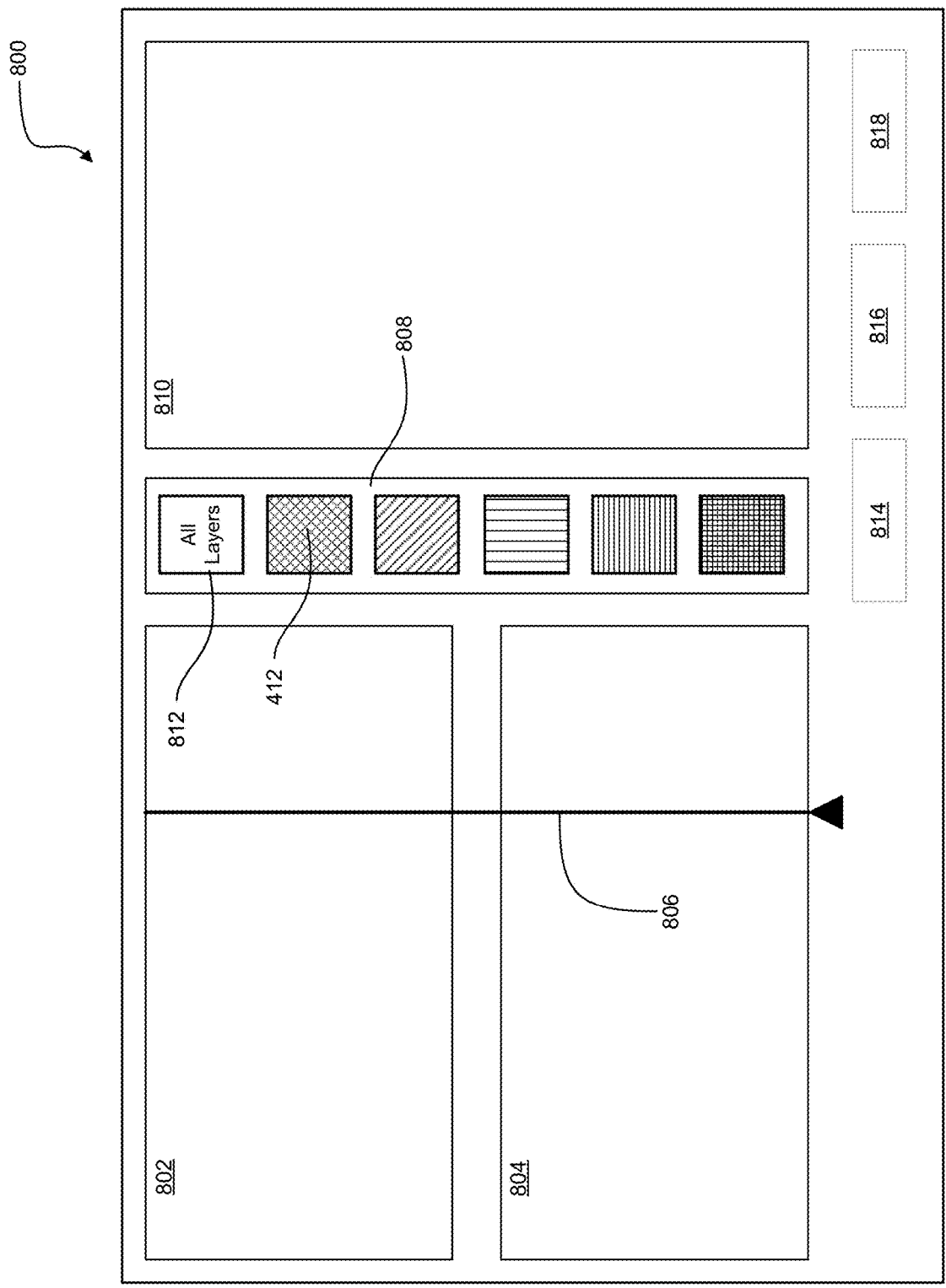
FIG. 8 illustrates an interface of displaying and animating pain entries in chronological order according to various embodiments of the disclosure.

With reference to FIG. 8, a summary screen 800 is shown to animate pain entries 312 in chronological order. Summary screen 800 comprises a pain intensity display 802 aligned over a coverage area display 804. Pain intensity display 802 may illustrate pain intensity over time (e.g., using a graphical representation similar to plot 704 of FIG. 7). Coverage area display 804 may illustrate the surface area of the body covered by pain (e.g., using a graphical representation similar to plot 714 of FIG. 7). A time cursor 806 may move from right to left across pain intensity display 802 and coverage area display 804. Time cursor 806 may be moved manually by a user or automatically during animation. The intersection of a line graph or data point in pain intensity display 802 with time cursor 806 may indicate the pain intensity experienced for the selected graphical pain representation 412 at a given time. The intersection of a line graph or data point in coverage area display 804 with time cursor 806 may indicate the pain coverage area over a body for the selected graphical pain representation 412 at a given time. Pain map 810 may display pain locations on a body by superimposing graphical pain representations 412 over body 606 as described above with reference to pain location screen 600 of FIG. 6. The pain mapping displayed in pain map 810 may correspond to the time selected by time cursor.

In various embodiments, graphical pain representation 412 may be selected in pain selection display 808. A user may select all layers by pressing button 812. A user may also select one or more graphical pain representations 412. Graphical pain representations 412 may be arranged vertically on screen with one graphical pain representations 412 for each pain type 410. Graphical pain representations 412 may be framed so that a user may scroll through graphical pain representation 412 to move the entries on and off screen. To access the non-visible buttons the user uses his or her finger to scroll the buttons up or down as needed to access all the choices. Summary screen 800 may display the total pain intensity for all pain entries 312 in pain intensity display 802 and the total coverage area in coverage area display 804 in response to all layers being selected. Summary screen may display the same information for individual pain entries 312 or a set of pain entries 312 in response to the desired pain entries 312 being selected.

In various embodiments, summary screen 800 may present pain entries 312 in an animated fashion. The animation may illustrate how pain changes over time. Start date and time interface 814 may comprise a "Starting Date/Time" button followed by a box to select a pain entry 312. End date and time interface 816 may comprise "Ending Date/Time" button followed by a box to select pain entry 312. Start animation interface 818 may comprise a "Start Animation" button configured to being animation when pressed. The animation may animate pain mappings in pain map 810 in chronological order beginning with a selected start pain entry 312 and ending at a selected end pain entry 312.

In various embodiments, summary screen 800 may allow a user or provider to quickly assess all of a patient's pain entries 312 on one screen in an animated fashion. The user may select the desired graphical pain representation 412 (or All Layers) and use animation interface 818 to visually map pain entries 312 for the selected graphical pain representations 412 on the front and back sides of the body 606 in sequence and for a selected time period.

The interactive pain-tracking system using electronic device 100 and process 200 enables users to electronically track, analyze, and map numerous individually distinct types of pain at different times. In that regard, the pain tracking system may accurately record and monitor pain a subject is suffering. The information may be more accurate than human memory and can be used to improve the basis for accurate diagnosis and/or treatment plans. The pain tracking system thus enables complete communication of pain to physicians, nurses, nurse practitioners, physical therapists, and physician assistants, and other health care professionals for treatment and monitoring of progress. The treatment and progress monitoring are based on the most accurate and complete pain-related information available, as the information may be recorded when experienced.

The interactive pain-tracking system using electronic device 100 and process 200 may assist in identifying pain improvement when two or more pain types are present. For example, a patient may claim to have pain with an intensity of 8/10 for six weeks. The patient may actually have 8/10 stabbing pain for 6 weeks, but burning pain may decrease from 8 to 0 over the course of the 6 weeks. Because the patient and healthcare provider are not noticing that the patient actually has multiple types of pain at the same time, the decrease in burning pain may not be recognized. The physician and patient may think that the patient's pain is the same or unchanging because no one appreciates that the burning pain has actually decreased. In that regard, the interactive pain tracking system may enable diagnosis when one pain is decreasing but overshadowed by another pain in the same area of the body.

The interactive pain-tracking system using electronic device 100 and process 200 may also assist in identifying pain improvement when pain intensity remains the same but coverage area shrinks over a time period. For example, a patient may claim to have pain with an intensity of 8/10 for six weeks. The coverage area of the pain may begin at 50% week one and decrease to 5% by week six. Because the patient and healthcare provider are not noticing that the patient actually has decreasing pain coverage area, the patient and doctor may erroneously believe the current course of treatment is not effective. The physician and patient may think that the patient's pain is the same or unchanging because no one appreciates that the pain area has actually decreased. In that regard, the interactive pain tracking system may enable diagnosis when pain intensity remains the same over time but coverage area of the pain decreases.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors. The processor is connected to a communication infrastructure (e.g., a communications bus, cross over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

In various embodiments, components, modules, and/or engines of the system (including process 200 and electronic device 100) may be implemented as micro-applications or micro-apps. Micro-apps are typically deployed in the context of a mobile operating system, including for example, a Palm mobile operating system, a Windows mobile operating system, an Android Operating System, Apple iOS, a Blackberry operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/groups/SNS/cloud-computing/cloud-def-v15.doc (last visited Feb. 4, 2011), which is hereby incorporated by reference in its entirety.

Any databases discussed herein may include relational, hierarchical, graphical, or object-oriented structure and/or any other database configurations. Common database products that may be used to implement the databases include DB2 by IBM (Armonk, N.Y.), various database products available from Oracle Corporation (Redwood Shores, Calif.), Microsoft Access or Microsoft SQL Server by Microsoft Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

Encryption may be performed by way of any of the techniques now available in the art or which may become available—e.g., Twofish, RSA, El Gamal, Schorr signature, DSA, PGP, PKI, GPG (GnuPG), and symmetric and asymmetric cryptosystems.

The computers discussed herein may provide a suitable website or other Internet-based graphical user interface which is accessible by users. In various embodiments, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server.

Additionally, components such as Access or Microsoft SQL Server, Oracle, Sybase, Informix MySQL, Interbase, etc., may be used to provide an Active Data Object (ADO) compliant database management system. In various embodiments, the Apache web server is used in conjunction with a Linux operating system, a MySQL database, and the Perl, PHP, and/or Python programming languages.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, VBScript, Macromedia Cold Fusion, COBOL, Microsoft Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an Internet based embodiment, an entirely hardware embodiment, or an embodiment combining aspects of the Internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. Reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method comprising:
   recording, by a processor, information pertaining to a plurality of episodes of pain experienced by a subject over time;
   recording, by the processor, a plurality of pain types corresponding to each episode of pain of said plurality of episodes of pain;
   recording, by the processor, a pain intensity corresponding to each pain type of said plurality of pain types for each episode of pain;
   recording, by the processor, information pertaining to a location of boundaries, in response to input encircling said boundaries on a body representation presented on a display of said subject, for each pain type for each episode of pain;
   configuring said processor to compute, using said information pertaining to the location of the boundaries on said body representation of said subject where each pain type for each episode of pain occurred, a coverage area, wherein (i) a surface area is calculated by said processor from said coverage area for each pain type for each episode of pain, (ii) each of said surface areas calculated is presented as a layer on said body representation on said display, (iii) each of said layers provides a graphical representation of said surface area at said location of one of said pain types for one of said plurality of episodes of pain and (iv) each of said layers is individually selectable for presentation on said display; and
   computing and selectively outputting a composite display of a temporal change, over time over which said subject experienced said plurality of episodes of pain, an identifier of each pain type for each episode of pain, said pain intensity corresponding to each pain type for each episode of pain, and said surface area of each pain type for each episode of pain, the computing and selectively outputting the composite display being conducted:
   (i) individually for a single pain type experienced by said subject over said plurality of episodes of pain and
   (ii) collectively for all pain types experienced by said subject over said plurality of episodes of pain, to provide a representation of overall effectiveness of a treatment plan for addressing said plurality of pain types over said plurality of episodes of pain.

2. The method of claim 1, further comprising:
   configuring said processor to identify the temporal change, over said plurality of episodes of pain, in (i) each pain type, (ii) said pain intensity corresponding to each pain type, and (iii) said surface area of each pain type.

3. The method of claim 1, wherein the processor, via said display, selectively outputs a graph showing said temporal changes in each pain type, including said pain intensity corresponding to each pain type and said surface area of each pain type over said plurality of episodes of pain.

4. The method of claim 1, wherein the processor, via said display, selectively outputs a series of body representations showing said temporal change in each pain type, including said pain intensity and said surface area corresponding to each pain type over said plurality of episodes of pain.

5. The method of claim 4, wherein the processor via said display, selectively outputs said series of body representations showing said temporal changes, with each body representation of the series of body representations including a plurality of layers and each layer of the plurality of layers representing a pain type and said surface area of said pain type, and having said pain intensity of said pain type associated with each layer.

6. An article of manufacture including a non-transitory, tangible computer-readable memory having instructions stored thereon that, in response to execution by a computer-based processor, cause the computer-based processor to perform operations comprising:
 recording, by the computer-based processor, information pertaining to each episode of a plurality of episodes of pain experienced by a subject over a period of time;
 recording, by the computer-based processor, a plurality of pain types corresponding to each episode of pain;
 recording, by the computer-based processor, a pain intensity corresponding to each pain type of said plurality of pain types for each episode of pain;
 recording, by the computer-based processor, information pertaining to a location of boundaries, in response to input encircling said boundaries on a body representation presented on a display of said subject, where pain type for each episode of pain occurred;
 computing, using said information pertaining to the location of the boundaries on said body representation of said subject where each pain type for each episode of pain occurred, a coverage area of said pain type, wherein (i) a surface area is calculated by said computer-based processor from said coverage area for pain type for each episode of pain, (ii) said surface area is presented as a layer on said body representation on said display, (iii) said layer provides a graphical representation of said surface area at said location of said pain type for said episode of pain and (iv) said layer is individually selectable for presentation on said display in connection with said pain intensity corresponding to said pain type to which said layer corresponds; and
 computing a temporal change, over said period of time, in said surface area and said pain intensity for said pain type over said plurality of episodes of pain.

7. The article of manufacture of claim 6, wherein said instructions cause the computer-based processor to perform further operations comprising:
 identifying the temporal change, over said period of time, in said surface area for each pain type and said pain intensity for each pain type over said plurality of episodes of pain.

8. The article of manufacture of claim 6, wherein said instructions cause the computer-based processor to perform further operations comprising:
 displaying, by the computer-based processor and via said display, said computed temporal change in said surface area for each pain type and said pain intensity for said pain type for each episode of pain of said plurality of episodes of pain.

9. The article of claim 7, wherein said instructions cause the computer-based processor to perform further operations comprising:
 displaying, by the processor and via said display, said temporal change in each pain type, said pain intensity for each pain type, and said surface area for each pain type for each episode of pain of said plurality of episodes of pain.

10. A system including a processor and a non-transitory, tangible, computer-readable medium storing instructions that, when executed, cause said processor to perform operations comprising:
 recording, by the processor, information pertaining to each episode of a plurality of episodes of pain experienced by a subject over a period of time, wherein each episode of pain comprises a plurality of pain types;
 recording, by the processor, information pertaining to a pain intensity of each pain type of said plurality of pain types for each episode of pain;
 recording, by the processor, information pertaining to a location of boundaries, in response to input encircling said boundaries on a body representation presented on a display of said subject, where each pain type of each episode of pain occurred;
 computing, using said information pertaining to the location of the boundaries on the body representation of said subject where each of said pain types of each of said plurality of episodes of pain occurred, a coverage area of each of said plurality of episodes of pain, wherein (i) a surface area is calculated by said processor from said coverage area for each pain type for each episode of pain, (ii) said surface area is presented as a layer on said body representation on said display, (iii) said layer provides a graphical representation of said surface area at said location of said pain type for said episode of pain, (iv) said layer is individually selectable for presentation on said display, and (v) said layer is displayed in association with said pain intensity corresponding to said pain type;
 computing a temporal change, over said period of time, in said pain intensity of said pain type and said surface area of said pain type over said plurality of episodes of pain; and
 displaying, for each pain type, said temporal change.

11. The system of claim 10, wherein said instructions cause said processor to perform further operations comprising:
 displaying, by said processor and via said display, said surface area and said pain intensity of each pain type in each episode of pain.

12. The system of claim 10, wherein said instructions cause the processor to perform further operations comprising:
 displaying, by said processor and via said display, said temporal change in said surface area and said pain intensity of each pain type over said plurality of episodes of pain.

13. The system of claim 12, wherein said instructions cause said processor to display said temporal change in said surface area and said pain intensity over said plurality of episodes of pain as graphs.

14. The system of claim 13, wherein said graphs provide a representation of an overall effectiveness of a treatment plan for addressing said plurality of pain types over said plurality of episodes of pain.

15. The system of claim 14, wherein said instructions further cause said processor to display said temporal change in said surface area and said pain intensity over said plurality of episodes of pain as a series of body representations.

16. The system of claim 15, wherein said series of body representations provide a representation of an overall effectiveness of a treatment plan for addressing said plurality of pain types over said plurality of episodes of pain.

17. The system of claim 12, wherein said instructions cause said processor to display said temporal change in said surface area and said pain intensity over said plurality of episodes of pain as a series of body representations.

18. The system of claim 17, wherein said instructions cause said processor to display said temporal change in said surface area and said pain intensity for said plurality of pain types.

19. The system of claim 17, wherein said series of body representations provide a representation of an overall effectiveness of a treatment plan for addressing said plurality of pain types over said plurality of episodes of pain.

* * * * *